United States Patent
Crosby

(10) Patent No.: US 10,247,836 B2
(45) Date of Patent: Apr. 2, 2019

(54) RESOLUTION CONTROL IN X-RAY FLUORESCENCE SPECTROSCOPY SYSTEMS

(71) Applicant: THERMO GAMMA-METRICS PTY LTD, Adelaide Airport (AU)

(72) Inventor: Bryan John Crosby, Adelaide (AU)

(73) Assignee: THERMO GAMMA-METRICS PTY LTD, Adelaide Airport (AU)

(*) Notice: Subject to any disclaimer, the term of this patent is extended or adjusted under 35 U.S.C. 154(b) by 732 days.

(21) Appl. No.: 14/969,857

(22) Filed: Dec. 15, 2015

(65) Prior Publication Data

US 2017/0168172 A1  Jun. 15, 2017

(51) Int. Cl.
| | |
|---|---|
| *H01J 35/16* | (2006.01) |
| *G01T 7/00* | (2006.01) |
| *G01N 23/223* | (2006.01) |
| *G01T 1/40* | (2006.01) |

(52) U.S. Cl.
CPC ........... *G01T 7/005* (2013.01); *G01N 23/223* (2013.01); *G01T 1/40* (2013.01); *G01N 2223/3037* (2013.01)

(58) Field of Classification Search
CPC .. G06F 3/04883; A47L 2201/04; A47L 11/33; G01N 2223/3037; G01N 23/00; G01N 23/30; G01N 23/22
See application file for complete search history.

(56) References Cited

U.S. PATENT DOCUMENTS

| | | | |
|---|---|---|---|
| 3,433,954 A | 3/1969 | Bowman | |
| 6,522,718 B2 | 2/2003 | Sato | |
| 9,775,574 B2 * | 10/2017 | Jones | ................... G01N 23/223 |
| 2008/0156996 A1 | 7/2008 | Nicolosi et al. | |
| 2015/0234060 A1 | 8/2015 | Rinsema et al. | |

FOREIGN PATENT DOCUMENTS

| | | |
|---|---|---|
| CN | 103808746 A | 5/2014 |
| DE | 10133676 A1 | 6/2002 |
| DE | 10200237 A1 | 7/2003 |
| DE | 112009000004 | 7/2010 |

OTHER PUBLICATIONS

Fernandes et al., "X-ray spectrometry with Peltier-cooled large area avalanche photodiodes", Nuclear Instruments and Methods in Physics Research B 213 (2004) 267-271.

* cited by examiner

*Primary Examiner* — Don Wong
(74) *Attorney, Agent, or Firm* — William R. McCarthy, III

(57) ABSTRACT

An embodiment of a method for restoring detector resolution in an X-Ray fluorescence instrument is described that comprises: measuring a resolution value of a detector in the X-Ray fluorescence instrument using a standard material at a first temperature; determining that the measured resolution value deviates from a target value; and adjusting the temperature of the detector to a second temperature that restores the resolution value of the detector to the target value, wherein the temperature is adjusted by an amount defined by a relationship of temperature change to the degree of deviation of detector resolution from the target value.

35 Claims, 6 Drawing Sheets

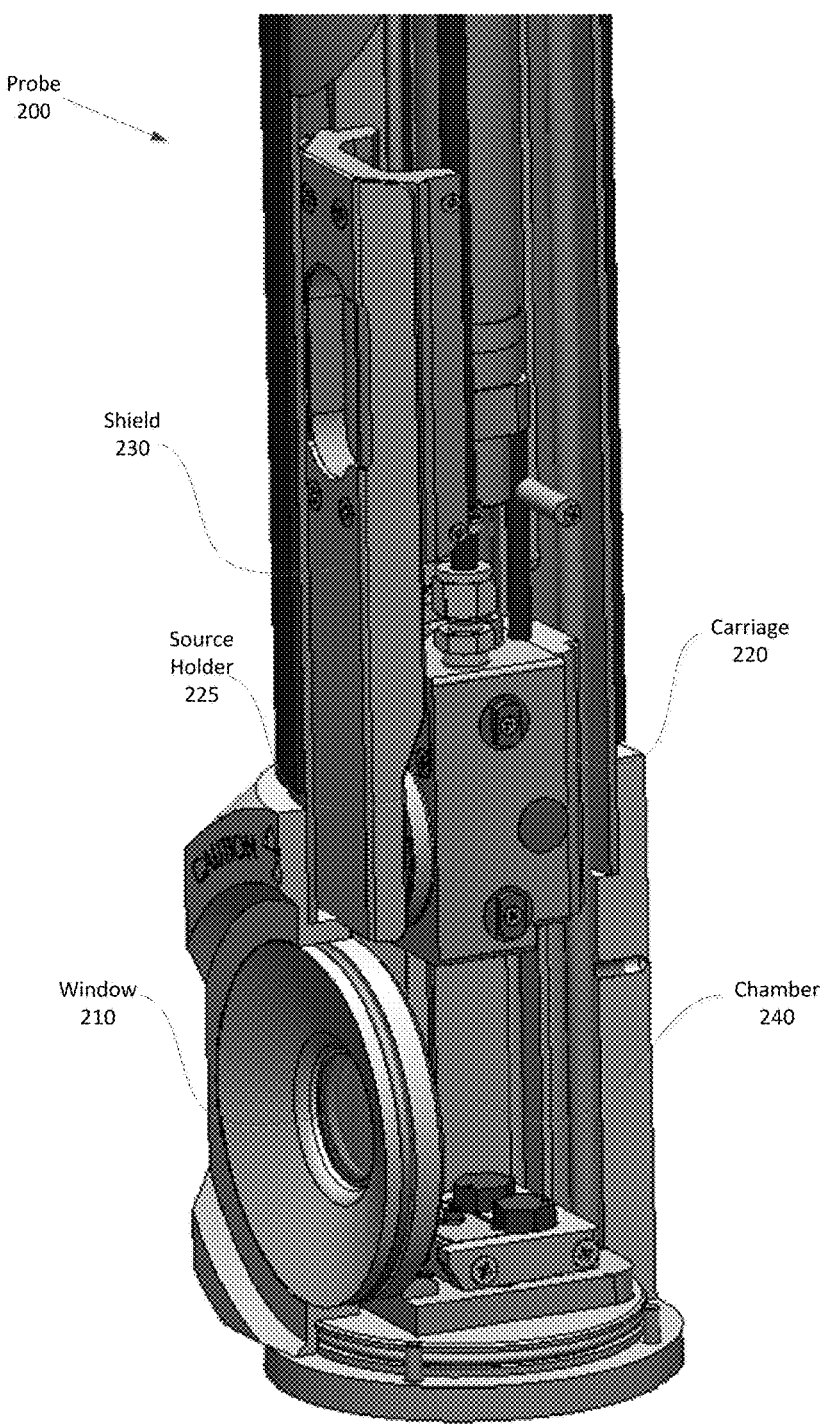

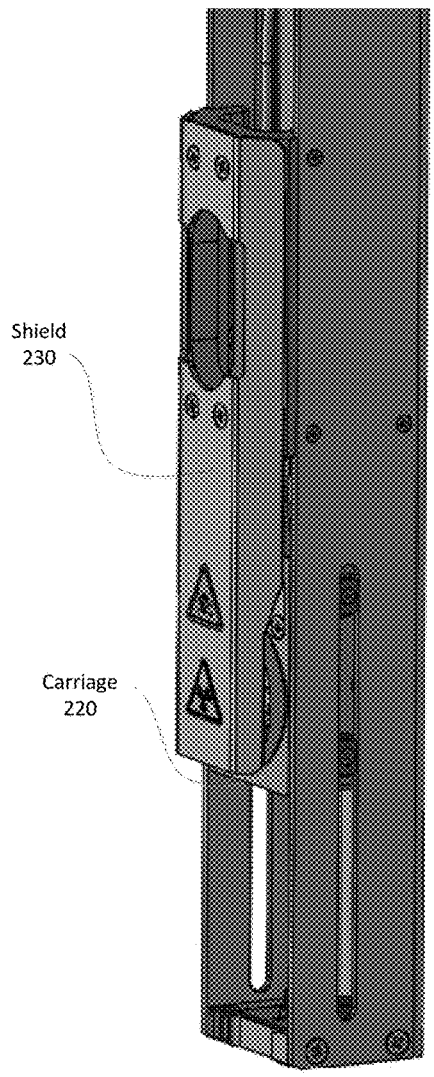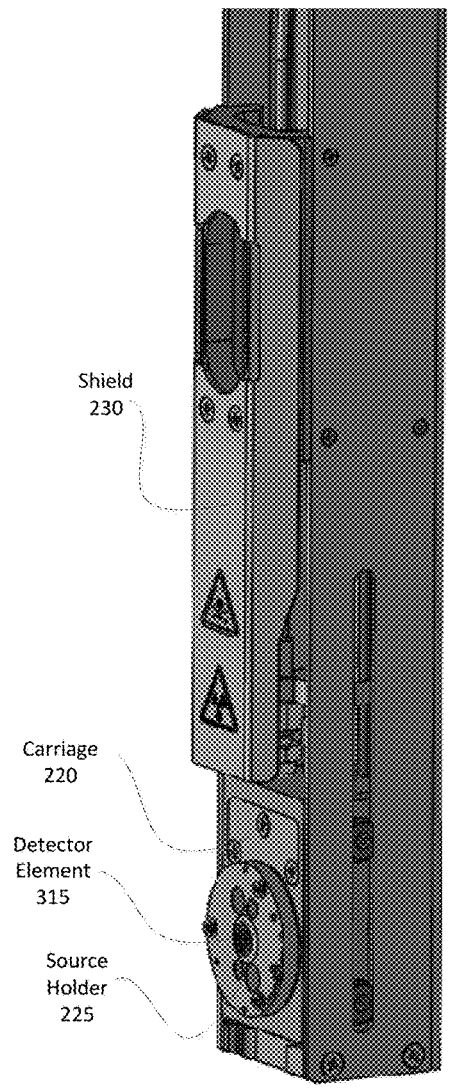

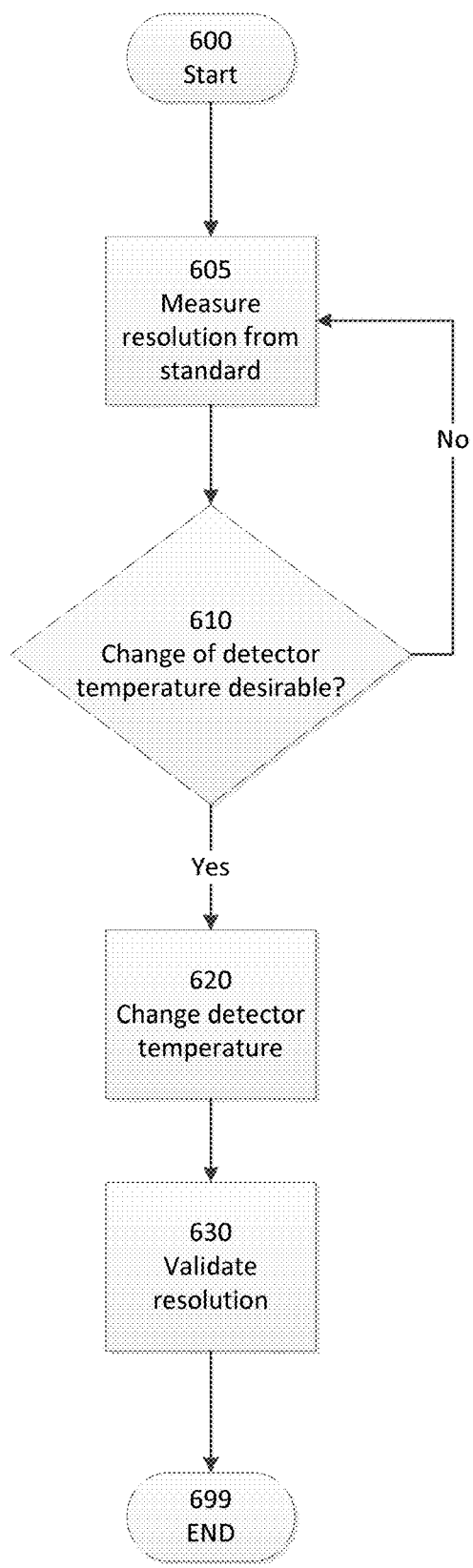

RESOLUTION CONTROL IN X-RAY FLUORESCENCE SPECTROSCOPY SYSTEMS

RELATED APPLICATIONS

The present application is related to U.S. patent application Ser. No. 14/969,766, titled "THERMAL CONTROL APPARATUS", and U.S. patent application Ser. No. 14/969,811, titled "XRF DETECTOR AND SOURCE CALIBRATION APPARATUS", both filed concurrently herewith, each of which is hereby incorporated by reference herein in its entirety for all purposes.

FIELD OF THE INVENTION

The invention relates to X-Ray Fluorescence Spectroscopy, multi-element probe devices, and methods for their use.

BACKGROUND OF THE INVENTION

It is generally appreciated that elemental and chemical analysis techniques have important applications to determine the composition of a material in various forms. X-Ray Fluorescence Spectroscopy (e.g. XRF) is a particularly useful technique for many applications of elemental and chemical analysis that includes a process of analyzing emissions from a test sample in response to exposure to X-Ray sources. The emissions from exposed samples comprise wavelength signatures that identify the elemental and chemical composition of the sample material enabling easy and rapid identification.

In particular applications, XRF instruments may be utilized in liquid environments using a probe in an analysis stream. More specifically some embodiments of such XRF instruments may utilize an X-Ray source and a Silicon Drift Device (SDD) for detection of the X-ray emissions. Historically, XRF detectors utilizing SDD components are maintained at a low set temperature because variation in temperature typically results in changes to the resolution of the XRF instrument. It is also appreciated that in certain applications the resolution of SDD detection components gradually degrade over time while the instrument is in continual operation, eventually reaching a point when the XRF instrument needs to be taken offline and restored back to its standard operating resolution. Such degradation of resolution affects the accuracy of analysis results produced by the XRF instrument which become unreliable due to the cumulative degradation of detector resolution over time of use.

In many embodiments the degradation is partly reversible via a process called thermal "annealing" that recovers the stable crystal structure of the detector, however the XRF instrument would typically need to be shut down and taken off-line for the annealing process resulting in disruption of operations that rely on the instruments to provide accurate measurements.

Therefore, it is appreciated that it is highly desirable to extend the useful time of the detector between periods of shut down for the annealing process while maintaining the accuracy of the analysis results for as long as possible. For example, it is desirable in many commercial environments to minimize the amount of time that an XRF instrument needs to be taken offline for repair and/or calibration allowing for near continuous operation while maintaining the accuracy and resolution of the instrument.

SUMMARY

Systems, methods, and products to address these and other needs are described herein with respect to illustrative, non-limiting, implementations. Various alternatives, modifications and equivalents are possible.

An embodiment of a method for restoring detector resolution in an X-Ray fluorescence instrument is described that comprises: measuring a resolution value of a detector in the X-Ray fluorescence instrument using a standard material at a first temperature; determining that the measured resolution value deviates from a target value; and adjusting the temperature of the detector to a second temperature that restores the resolution value of the detector to the target value, wherein the temperature is adjusted by an amount defined by a relationship of temperature change to the degree of deviation of detector resolution from the target value.

Also, an embodiment of an X-Ray fluorescence instrument is described that comprises a source adapted to direct X-ray radiation at a standard material; a detector adapted to collect emissions responsive to the X-ray radiation from the standard material, wherein the detector is maintained at a first temperature; and a controller adapted to: measure a resolution value of the detector using the collected emissions; determine that the measured resolution value deviates from a target value; and adjust the temperature of the detector to a second temperature that restores the resolution value of the detector to the target value, wherein the temperature is adjusted by an amount defined by a relationship of temperature change to the degree of deviation of detector resolution from the target value.

The above embodiments and implementations are not necessarily inclusive or exclusive of each other and may be combined in any manner that is non-conflicting and otherwise possible, whether they are presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 120 appears first in FIG. 1). All of these conventions, however, are intended to be typical or illustrative, rather than limiting.

FIG. 2 is a simplified graphical representation of one embodiment of a probe that includes a source holder, a carriage and a shield;

FIGS. 3A and 3B are simplified graphical representations of one embodiment of the probe of FIG. 2 with the carriage in a first position behind the shield and in a second position below the shield;

FIG. 6 is a functional block diagram of one embodiment of a method for adjusting resolution by changing a detector temperature.

Like reference numerals refer to corresponding parts throughout the several views of the drawings.

DETAILED DESCRIPTION OF EMBODIMENTS

As will be described in greater detail below, embodiments of the described invention include XRF systems and methods for addressing resolution variations that occur in response to damage. More specifically, embodiments include adjusting temperature parameters to compensate for resolution changes due to damage to the detector without taking the instrument offline. For example, temperature adjustments can be made to the detector element to maintain a target resolution in XRF instruments that utilize SDD detectors with damage accumulated over time of use. In the present example, the temperature adjustments can be made while the XRF instrument is in operation to restore resolution to a desired target resolution without taking the instrument offline. In the described embodiments, no more than 10 minutes of downtime per day in normal operation is desirable.

Some or all of the embodiments described herein may include one or more elements for operational control of an XRF instrument. For example, embodiments may include one or more processor, controller, and/or computer elements that execute control logic, data acquisition, and/or data processing operations for the XRF instrument. Also in the described embodiments, XRF instruments may include one or more probe elements for directing X-Rays at a sample and collecting emissions from the sample, as well as one or more elements for detecting the emitted radiation (e.g. SDD).

Figure 1:
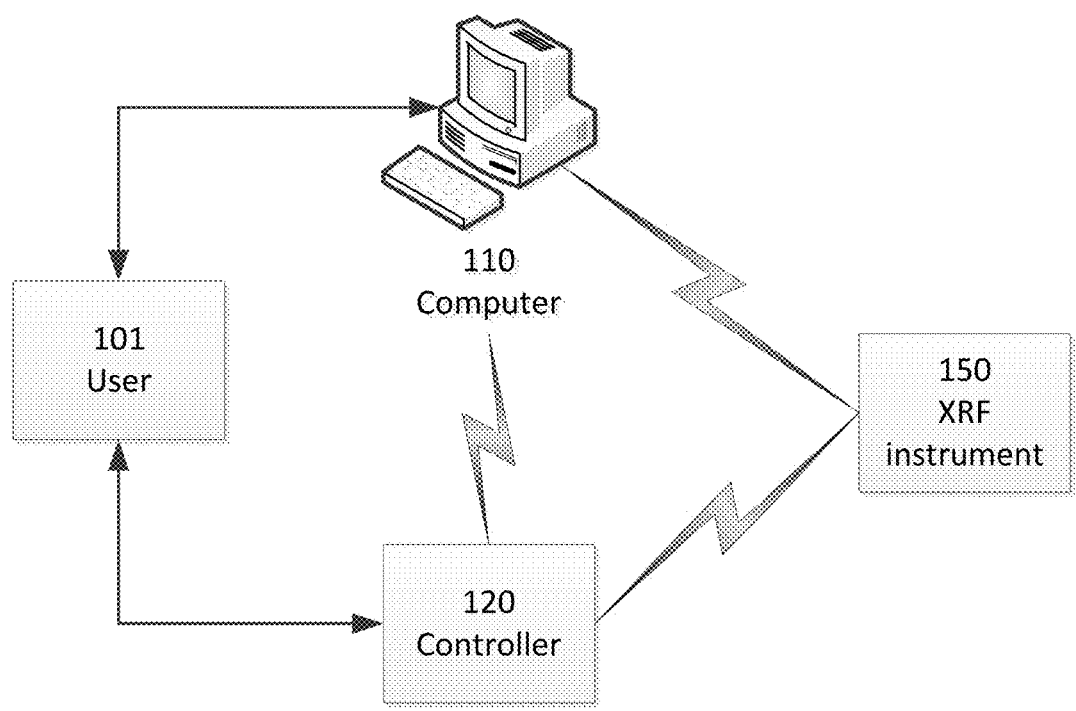
FIG. 1 is a simplified graphical representation of one embodiment of a an XRF instrument under control of a computer and/or controller.

FIG. 1 provides a simplified illustrative example of XRF instrument 150 that is in network communication with computer 110 and/or controller 120. FIG. 1 also illustrates user 101 capable of interacting with computer 110 of controller 120 as well as a network connection between computer 110 and controller 120.

Computer 110 may include any type of computer platform such as a workstation, a personal computer, a server, or any other present or future computer. Computers typically include known components such as a processor, an operating system, system memory, memory storage devices, input-output controllers, input-output devices, and display devices. Display devices may include display devices that provides visual information, this information typically may be logically and/or physically organized as an array of pixels. An interface controller may also be included that may comprise any of a variety of known or future software programs for providing input and output interfaces such as for instance interfaces. For example, interfaces may include what are generally referred to as a "Graphical User Interface" (GUI) that provides one or more graphical representations to a user. Interfaces are typically enabled to accept user inputs by means of selection or input known to those of ordinary skill in the related art.

In the same or alternative embodiments, applications on a computer may employ an interface that is referred to as a "command line interface" (CLI). CLIs typically provide a text based interaction between the application and a user. Typically, command line interfaces present output and receive input as lines of text through display devices.

Those of ordinary skill in the related art will appreciate that interfaces may include one or more GUIs, CLIs or a combination thereof.

It will be understood by those of ordinary skill in the relevant art that there are many possible configurations of the components of a computer and that some components that may typically be included in computer may also include cache memory, a data backup unit, and many other devices. A processor may be a commercially available processor such as a Core™ processor made by Intel Corporation, a SPARC® processor made by Sun Microsystems, an Athlon™ or FX processor made by AMD corporation, or it may be one of other processors that are or will become available. Some embodiments of a processor may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows® type operating system from the Microsoft Corporation; the Mac OS X operating system from Apple Computer Corp.; a Unix® or Linux-type operating system available from many vendors or what is referred to as an open source; another or a future operating system; or some combination thereof. An operating system interfaces with firmware and hardware in a well-known manner, and facilitates processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium such as a resident hard disk or tape, an optical medium such as a read and write compact disc, or other memory storage device. The processor typically reads from, and/or writes to memory storage devices that may include any of a variety of known or future devices, including a compact disk drive, a tape drive, a removable hard disk drive, USB or flash drive. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers could include controllers for any of a variety of known display devices for presenting information to a user, whether a human or a machine, whether local or remote. In the presently described embodiment, the functional elements of a computer communicate with each other via a system bus. Some of these communications may be accomplished in alternative embodiments using network or other types of remote communications.

As will be evident to those skilled in the relevant art, an instrument control and data processing application, if implemented in software, may be loaded into and executed from system memory and/or a memory storage device. All or portions of the instrument control and data processing applications may also reside in a read-only memory or similar device of the memory storage device, such devices not requiring that the instrument control and data processing applications first be loaded through input-output controllers. It will be understood by those skilled in the relevant art that the instrument control and data processing applications, or portions of it, may be loaded by a processor in a known manner into system memory, or cache memory, or both, as advantageous for execution.

Also a computer may include one or more library files, experiment data files, and an internet client stored in system memory. In the described embodiments, an internet client may include an application enabled to accesses a remote service on another computer using a network that may for instance comprise what are generally referred to as "Web Browsers". In the present example some commonly employed web browsers include Microsoft® Internet Explorer or Edge available from Microsoft Corporation, Mozilla Firefox® from the Mozilla Corporation, Safari from Apple Computer Corp., or other type of web browser currently known in the art or to be developed in the future. Also, in the same or other embodiments an internet client may include, or could be an element of, specialized software applications enabled to access remote information via a network.

A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

As described above, embodiments of the invention include systems and methods for implementing a process that includes measurement of instrument resolution at regularly programmed and/or user defined (e.g. via user selection of a button, GUI element, etc.) times. If an unacceptable deviation from a target resolution or target range of resolution is detected, an adjustment of temperature parameters to compensate for the deviation is made to restore the resolution to the acceptable level (e.g. process sometimes referred to as Automatic Resolution Maintenance (ARM)). For example, in some embodiments a deviation of about 3 eV from a target resolution would be considered undesirable and would initiate resolution adjustment to compensate for the damage causing the deviation.

In some or all of the described embodiments one or more "standards" may be employed for the resolution measurement. The term "standard" as used herein generally refers to a material with known elemental and/or chemical composition that provides a distinct emission signature in response to exposure to X-rays. In typical embodiments the emission signature produced from a properly calibrated embodiment of XRF instrument 150 is known and thus test measurements produce signatures that can be compared to the known emission signature and correlated to a degree of degradation of the detector. For example, measurement of a standard by the XRF instrument should return the target resolution if the instrument is properly calibrated (e.g. little or no deviation). In the event that detector damage has occurred, there is a quantifiable difference in the measured resolution from the standard from the known standard resolution. In the presently described example, the standard may include a composition of mineral and polymer known to emit a particular spectral profile in response to exposure to the X-Rays from the isotope source.

In the embodiments described herein, the standard is positioned in an analysis zone of the instrument that may include an internal zone (e.g. standard positioned within the internal environment and facing components of a probe element of XRF instrument 150) and/or external zone outside of a probe element of XRF instrument 150. When a standard is properly positioned in the analysis zone, the probe element of XRF instrument 150 exposes the standard to X-Ray radiation and detects the emitted radiation from the standard that is then interpreted by software executed by controller 120 and/or computer 110 elements that compute the measured resolution and compares the measured resolution to the expected resolution associated from the standard (e.g. the target resolution) to determine if a deviation exists. For example, the target resolution may include a value in a range of about 140 eV to about 200 eV, such as a value of about 170 eV. In cases where a deviation does exist with a degree of deviation that exceeds an acceptable range, then controller 120 and/or computer 110 elements initiate a compensation mechanism. In the described example, the target value is specified in a configuration file stored in controller 120 and/or computer 110 and an acceptable range from the target value is one that is small enough that accuracy of measurement is still acceptable. In the present example the range may be within 3 eV of the target value. Additional examples of an internal standard and positional relationship within a probe of XRF instrument

150 is described in U.S. patent application Ser. No. 14/969,766, titled "THERMAL CONTROL APPARATUS", and U.S. patent application Ser. No. 14/969,811, titled "XRF DETECTOR AND SOURCE CALIBRATION APPARATUS", each of which is incorporated by reference above.

FIG. 2 provides an illustrative example of an embodiment of probe 200 that includes window 210, carriage 220, source holder 225, shield 230, and chamber 240. In the example of FIG. 2, carriage 220 may include an SDD detector that may be translatable vertically along an axis of probe 200 so that source holder 225 is in a first position opposite shield 230 or in a second position opposite window 210. FIG. 3A provides an additional example of carriage 220 in the first position and FIG. 3B provides an additional example of carriage 220 in the second position. FIG. 3B also illustrates detector element 315 positioned in a central portion of source holder 225. In the examples of FIGS. 2, 3A, and 3B, shield 230 may include an internal standard element positioned so that the internal standard is in an analysis position and exposed to the X-Rays from source holder 225 when carriage 220 in is the first position. Also, source holder 225 may include elements to limit the radiation detected so that only the emitted radiation from the internal standard is sensed by the SDD detector positioned within carriage 220.

In the embodiments described herein, source holder 225 includes one or more isotope sources such as Pu238, Cd109, Am241, Fe55, or Cm244. It will be appreciated by those of ordinary skill in the art that other isotope sources are also suitable and thus the list of sources should not be considered as limiting.

Also in the embodiments described herein the compensation mechanism includes temperature adjustments of the detector element that changes the gain of the detector that in turn affects resolution. For example, the relationship of temperature to resolution may be calculated (e.g. by generating a mathematical model after each annealing event) using a "Full Width Half Maximum" (e.g. FWHM) function to calculate the measured resolution. The temperature adjustment may be made by cooling the detector to restore resolution to the target value or within a range of values using a thermoelectric cooling device (e.g. Peltier device), Nitrogen, or other strategy for cooling known in the related art. For example, a 4° change of detector temperature from −31° C. to −35 ° C. can result in a resolution improvement of about 15 eV. Also, the lower detector temperature can result in an improved rate of degradation (e.g. the rate of degradation is slower at the lower temperature).

Figure 4:
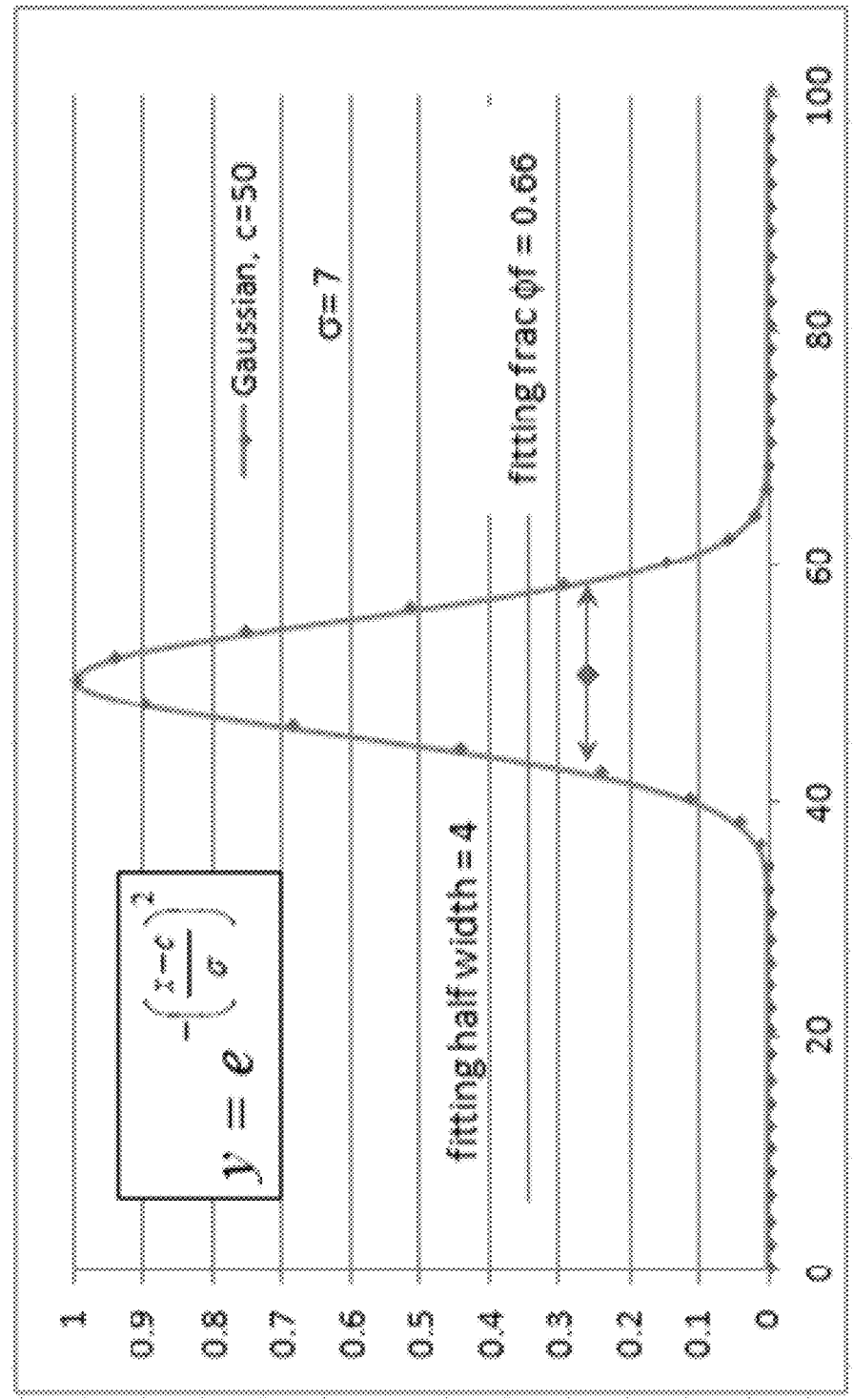
FIG. 4 is a simplified graphical representation of one embodiment of a Gaussian curve.

In some or all of the described embodiments the FWHM for resolution may be calculated using mathematical functions known to those of ordinary skill in the art. For example, FWHM is a parameter commonly used to describe the width of a peak on a spectrum and the formula used to calculate FWHM depends, at least in part, on the shape of the peak or curve (e.g. Gaussian, Lorentzian, Welch, Connes, etc.). In the present example a variety of FWHM formulas may be chosen for the calculation and it is not critical which algorithm is used as long as the same algorithm is consistently used for the measurements. FIG. 4 provides an illustrative example of a Gaussian curve where the relationship of FWHM to standard deviation (e.g. σ) may follow the following formula:

$$FWHM = 2\sqrt{\ln(2)}\sigma \approx 2.354\sigma$$

In some cases, simple filtering may be performed prior to calculation using the FWHM function that for some functions may improve results, however it is not necessarily required.

For example the filtering function may include:

$$y(x) = Y(x) - b(x)$$

$Y(x)$ is the raw spectrum, x is the energy, $y(x)$ is the background corrected spectrum and $b(x)$ is the accepted background correction.

$y(x)$ is assumed to be of the form:

$$y(x) = Ae^{d(c-x)^2}$$

take logs $$\ln(y(x)) = \ln(A) + d(c-x)^2 = \ln(A) + dc^2 - 2dcx + dx^2$$

which is in now an equation solvable as a series of linear equations.

The optimization parameter for the fitting routine would be Chi-square $$Z^2 = \sum_{i=1}^{N} \frac{(O_i - Y_i)^2}{Y_i}$$

The Observed values are $O_i$, and the $Y_i$ are the modeled values for $x_i$=the bins corresponding energy values. The fitting is optimized for the range of values around the central peak down to those points just less than the FWHM bounds. Standard fitting routines may be used.

In some embodiments, after an initial setup or an annealing event, one or more preparation steps should be performed prior to operation and execution of the ARM process. For example, the relationship of detector temperature to the resolution may need to be established through mathematical modeling. In the described embodiments the modeling may include a linear or non-linear function so that the resolution correction can be determined rapidly. In some embodiments a look up table may be generated that, for example, provides an association between a correction value for resolution improvement at a reference temperature. The parameters for the mathematical modeling may be derived by making resolution measurements through a series of temperatures that may include any range of temperature within a range of −20 to −60° C. For example, the control software may change the temperature of the detector by some increment and acquire the resolution value once the temperature has been stable for a period of time (e.g. 1 minute).

In the described embodiments the relationship between the resolution and temperature may be expressed as:

$$R = R_0 + Se^{C(T-T_0)}$$

As described above, measurements are taken through a series of temperature points. In some embodiments a minimum number of temperature measurements are required to produce accurate results where, for example, at least 4 measurements may be required.

Subsequently, the estimated detector temperature can be used to estimate the next temperature using the following:

$$T = T_0 + \frac{\ln((R - R_0)/S)}{C}$$

In practice the values of the 4 parameters used in the equations vary slightly according to the history of the detector, hence the parameter values can be determined by updating the equation after each measurement at a different temperature. In order to minimize errors associated with changes in temperature, the ratio of old to target resolution (RT) may be used to determine the new temperature. A fitting routine minimizes the mean square deviation between measured and fitted parameters.

Figure 5:
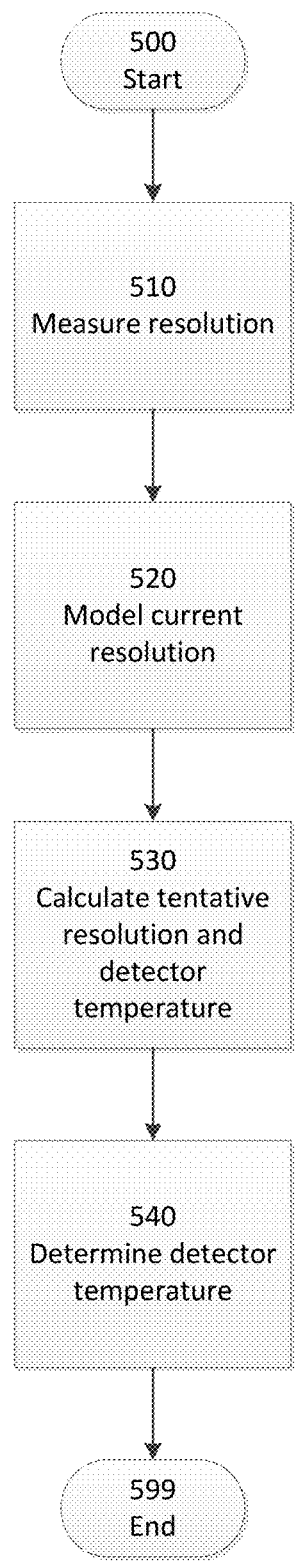
FIG. 5 is a functional block diagram of one embodiment of a method for determining a relationship between resolution and temperature.

FIG. 5 provides an illustrative example of a process for determining the relationship between values for detector temperature and values for resolution. First the process begins at step 500 and ends with step 599. At step 510 the control software measures actual resolution $R_A$ at each temperature point. Next at step 520, the control software calculates modeled current resolution using:

$$R_C = R_0 - Se^{C(T_D - T_v)}$$

At step 530, the control software uses the Target Ratio to calculate first the tentative resolution $R_t$ and then the detector temperature using:

$$R_t = R_C * \frac{R_T}{R_A}$$

Last, at step 540 the control software determines detector temperature values using:

$$T_D = T_0 + \frac{\ln((R_t - R_0)/S)}{C}$$

In this way, although the initial estimate may be wrong by a small amount, it is estimated to take the detector to within 0.5 eV of the target resolution after only the first attempt. After an annealing however, the equation may be less accurate and the equation can be further built up over subsequent measurements and range.

During normal operation of the embodiments of XRF instrument 150 described herein the detector temperature of probe 200 is maintained until the resolution has changed by more than an acceptable amount. For example, the measurement of resolution using the internal standard is performed at the same time every day or week at which time a determination is made regarding whether a resolution correction is desirable by changing the detector temperature. In the described example, if the detector resolution has changed by more than 3 eV and the standard error in the measurement is less than 1 eV, then the temperature is changed according to the degree of resolution correction required to return to a target resolution value.

FIG. 6 provides an illustrative example of a method for performing ARM that begins with step 600 and ends at step 699. In step 605 the ARM process measures resolution of the detector using a standard. In the described embodiments, step 605 occurs on a regular basis and is initiated by certain events or conditions. For example, step 605 may be initiated by control software (e.g. executed by the controller 120 and/or computer 110) that sends out a command to obtain a resolution measurement at specific points of time that includes weekly intervals or points of time during a calendar week (e.g. a daily measurement). In some cases the points in time include a selection by user 101 of days and/or times or may include a schedule preset by a manufacturer or defined by protocols, etc. In the described example, any of the points in time may be overridden by user selection to cancel or re-define for a new point in time.

In some embodiments, if the ARM process has occurred within a recent time period then the initiation of step 605 may be automatically overridden. In the described example, such a time period may include the smaller of:
1) 75% of the smallest selected interval; or
2) 1.7 days.

Alternatively, user 101 may select an immediate initiation of step 605 regardless of schedule or when the last process was executed. In the same or alternative embodiments, carriage 220 may be translated to the first position as illustrated in FIG. 3A for the purpose of preventing X-ray radiation from exiting probe 200 through window 210 whereupon the control software may initiate step 605 given that carriage 220 and the internal standard are in the appropriate positional relationship to execute the ARM measurement (e.g. carriage 220 is not translated specifically to initiate step 605). Additionally, the control software may initiate step 605 each time XRF instrument 150 powers up or if the instrument has been powered down for a period that exceeds a set amount of time. Lastly, the control software may initiate step 605 after temperature adjustment from a previous iteration of the ARM process to determine whether the resolution of the detector at the new temperature is at the desired target level.

As described above, the control software instructs XRF instrument 150 to expose a standard element to X-Ray radiation from source holder 225 (e.g. either an internal standard with carriage 220 in the first position or an external standard through window 210 with carriage 220 in the second position) and receive the emissions from the standard via the SDD detector positioned in carriage 220. The control software or other firmware/software then processes the signals from the detected emissions to generate a resolution value. In the embodiments described herein the resolution may be calculated using a variety of possible algorithms but needs to be consistent for any standard used.

As described above, it is expected that the detector resolution changes with time of use due to detector degradation. Decision element 610 indicates whether a change of detector temperature is desirable. In some embodiments, at step 610 the control software may check to determine if one or more pre-requisites exist indicating that a temperature change is warranted. In some embodiments, if one or more pre-requisites are not met the method returns to step 605 for measurement at the designated time. For example, a first pre-requisite includes determining that the number of previous resolution measurements made at the same temperature falls within a desired range since the last annealing event occurred and/or since the last temperature adjustment, and may include a range between 5 and 20 resolution measurements. In other words, if for instance only 3 resolution measurements have been taken since the last annealing event then the control software would not change the temperature in favor of taking additional resolution measurements.

A second pre-requisite includes determining that the latest resolution measurement shows that the resolution has degraded out of the acceptable range (e.g. 3 eV), and a third pre-requisite includes determining that the standard error in resolution measurement is at most ⅓ of the acceptable range (e.g. standard error <⅓ of 3 eV<1 eV).

Standard error may be calculated as the standard deviation/sqrt (number of measurements) using the following (n=number of measurements):

$$SE = \sigma/\sqrt{n}$$

As described herein, the resolution of the detector changes with time that XRF instrument 150 is operational. In some embodiments, the value for current resolution can be determined by linear least squares fit to resolution against time. Thus the slope will not bias estimate for current resolution.

For example, the relevant equations may include:

$$ss_{xx} = \sum_{i=1}^{n}(x_i - \bar{x})^2$$
$$= \left(\sum_{i=1}^{n} x_i^2\right) - n\bar{x}^2$$

$$ss_{yy} = \sum_{i=1}^{n}(y_i - \bar{y})^2$$
$$= \left(\sum_{i=1}^{n} y_i^2\right) - n\bar{y}^2$$

$$ss_{xy} = \sum_{i=1}^{n}(x_i - \bar{x})(y_i - \bar{y})$$
$$= \left(\sum_{i=1}^{n} x_i y_i\right) - n\bar{x}\bar{y}.$$

In terms of the sums of squares, the regression coefficient b is given by $$b = \frac{\text{cov}(x, y)}{\sigma_x^2} = \frac{ss_{xy}}{ss_{xx}},$$

and a is given in terms of b using $$a = \bar{y} - b\bar{x},$$

In the linear fit:

$$\hat{y}_i \approx a + bx_i,$$

the standard error in a is given as $$SE(a) = s\sqrt{\frac{1}{n} - \frac{\bar{x}^2}{ss_{xx}}}$$

In order to determine both the estimated current resolution and the standard error in that calculation, the time of each resolution measurement must also be recorded. In some or all of the described embodiments the easiest value to use for regression is the time since the measurement was taken. Then the value of SE(a) is also the SE of current estimate of resolution.

As described above, if the resolution measurement indicates that a temperature change is desirable, as illustrated in step 620 the control software initiates the temperature change according to the degree of change needed to bring the resolution back to the desired target.

In the embodiments described herein, the detector temperature is measured directly. In some embodiments the set temperature used by the control software may have a small offset from the measured detector temperature when, for instance a proportional controller used to drive thermoelectric cooling device (e.g. a Peltier cooler). For example, in order to achieve the desired detector temperature, a compensating offset will need to be applied when setting the temperature for the SDD. The offset is a function of temperature and can also be learned during resolution measurements.

In some cases the form of the equation may include:

$$T_s = T_D + \text{Offset}(T_D)$$

As illustrated in step 630, after the detector temperature has been changed one or more resolution measurements are taken by the control software to ensure the target resolution has been achieved.

As described herein, annealing includes a physical process whereby damaged detectors are left at a temperature that allows a thermal process to recover the stable crystal structure of the detector. In some embodiments, the annealing occurs passively if a detector is allowed to warm to room temperature when power has been turned off to XRF instrument 150. Alternatively, XRF instrument 150 may remain powered up if control software initiates a temperature change to allow detector temperature to be monitored while warming.

In some embodiments the annealing process may be unaided by external heater, however in the same or alternative embodiments if active annealing is implemented then an external heater may be used. For example, an annealing temperature of about 45° C. may be desirable and thermoelectric heating elements may be used that are known in the art that can be powered via a low voltage power supply. In the present example, a sensor typically used to measure the temperature of the liquid environment outside of probe 200 or other sensor can be used to control the power to the heater.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

What is claimed is:

1. A method for restoring detector resolution in an X-Ray fluorescence instrument, comprising:
    measuring a resolution value of a detector in the X-Ray fluorescence instrument using a standard material at a first temperature;
    determining that the measured resolution value deviates from a target value; and
    adjusting the temperature of the detector to a second temperature that restores the resolution value of the detector to the target value, wherein the temperature is adjusted by an amount defined by a relationship of temperature change to the degree of deviation of detector resolution from the target value.

2. The method of claim 1, wherein:
    the target value comprises a value in a range of about 140 eV to about 200 eV.

3. The method of claim 1, wherein:
    the standard material is positioned in an internal space of a probe of the X-Ray fluorescence instrument.

4. The method of claim 1, wherein:
    the standard material is positioned in outside of a probe of the X-Ray fluorescence instrument.

5. The method of claim 1, further comprising:
    iteratively repeating the step of measuring at a defined interval.

6. The method of claim 5, wherein:
    the defined interval comprises a daily or weekly interval.

7. The method of claim 1, wherein:
    the temperature of the detector is adjusted while the X-Ray fluorescence instrument is in operation.

8. The method of claim 1, wherein:
the temperature is adjusted when the measured resolution value deviates from a target value by about 3 ev.

9. The method of claim 1 wherein:
the temperature is adjusted when the measured resolution comprises a standard error of no more than ⅓$^{rd}$ of an acceptable resolution range.

10. The method of claim 1, further comprising:
measuring the resolution value of the detector using the standard material at the adjusted temperature.

11. The method of claim 1, wherein:
the step of determining further comprises determining that a minimum number of the resolution measurements have been made at the first temperature since annealing or since a previous temperature adjustment.

12. The method of claim 11, wherein:
the minimum number includes 5 resolution measurements.

13. The method of claim 1, wherein:
the relationship of temperature change to the degree of deviation of detector resolution from the target value is computed from a series of resolution measurements at different temperatures.

14. The method of claim 13, wherein:
the series of resolution measurements at different temperatures includes at least 4 measurements.

15. The method of claim 13, wherein:
the series of resolution measurements at different temperatures include any range of temperature within a range of about −20 to −60° C.

16. The method of claim 1, wherein:
the detector comprises a silicon drift detector that accumulates damage over time of use, wherein the damage degrades the resolution value of the detector.

17. The method of claim 1, wherein:
the standard comprises a composition of mineral and polymer known to emit a particular spectral profile in response to exposure to X-Ray radiation.

18. A X-Ray fluorescence instrument, comprising:
a source adapted to direct X-ray radiation at a standard material;
a detector adapted to collect emissions responsive to the X-ray radiation from the standard material, wherein the detector is maintained at a first temperature; and
a controller adapted to:
  measure a resolution value of the detector using the collected emissions;
  determine that the measured resolution value deviates from a target value; and
  adjust the temperature of the detector to a second temperature that restores the resolution value of the detector to the target value, wherein the temperature is adjusted by an amount defined by a relationship of temperature change to the degree of deviation of detector resolution from the target value.

19. The instrument of claim 18, further comprising:
a shield that holds the standard in a positional relationship with the source and the detector.

20. The instrument of claim 18, wherein:
the target value comprises a value in a range of about 140 eV to about 200 eV.

21. The instrument of claim 18, wherein:
the target value is specified in a configuration file stored in the controller.

22. The instrument of claim 18, wherein:
the controller is adapted to iteratively repeat the step of measuring at a defined interval.

23. The instrument of claim 22, wherein:
the defined interval comprises a daily to weekly interval.

24. The instrument of claim 18, wherein:
the temperature of the detector is adjusted while the X-Ray fluorescence instrument is in operation.

25. The instrument of claim 18, wherein:
the temperature is adjusted when the measured resolution value deviates from a target value by about 3 ev.

26. The instrument of claim 18, wherein:
the temperature is adjusted when the measured resolution comprises a standard error of no more than ⅓$^{rd}$ of an acceptable resolution range.

27. The instrument of claim 18, wherein:
the controller is further adapted to measure the resolution value of the detector using the standard material at the adjusted temperature.

28. The instrument of claim 18, wherein:
the controller is further adapted to determine that a minimum number of the resolution measurements have been made at the first temperature since annealing or since a previous temperature adjustment.

29. The instrument of claim 28, wherein:
the minimum number includes 5 resolution measurements.

30. The instrument of claim 18, wherein:
the relationship of temperature change to the degree of deviation of detector resolution from the target value is computed from a series of resolution measurements at different temperatures.

31. The instrument of claim 30, wherein:
the series of resolution measurements at different temperatures includes at least 4 measurements.

32. The instrument of claim 30, wherein:
the series of resolution measurements at different temperatures include any range of temperature within a range of about −20 to −60° C.

33. The instrument of claim 18, wherein:
the detector comprises a silicon drift detector that accumulates over time of use, wherein the damage degrades the resolution value of the detector.

34. The instrument of claim 18, wherein:
the second temperature is different from the first temperature.

35. The instrument of claim 18, wherein:
the standard comprises a composition of mineral and polymer known to emit a particular spectral profile in response to exposure to X-Ray radiation.

* * * * *